(12) United States Patent
Squartini et al.

(10) Patent No.: US 9,753,022 B2
(45) Date of Patent: Sep. 5, 2017

(54) METHOD AND DEVICE FOR ASSESSING THE LEVEL OF MICROBIAL ACTIVITY OF SOIL

(75) Inventors: Andrea Squartini, Padua (IT); Giuseppe Concheri, Camposampiero (IT); Stefano Tiozzo Netti, Sottomarina (IT)

(73) Assignee: UNIVERSITA' DEGLI STUDI DI PADOVA, Padua (IT)

( * ) Notice: Subject to any disclaimer, the term of this patent is extended or adjusted under 35 U.S.C. 154(b) by 731 days.

(21) Appl. No.: 14/125,380

(22) PCT Filed: Jun. 13, 2012

(86) PCT No.: PCT/IB2012/001157
§ 371 (c)(1),
(2), (4) Date: Jan. 28, 2014

(87) PCT Pub. No.: WO2012/140523
PCT Pub. Date: Oct. 18, 2012

(65) Prior Publication Data
US 2014/0216144 A1    Aug. 7, 2014

(30) Foreign Application Priority Data
Jun. 13, 2011 (IT) .................. VI2011A0154

(51) Int. Cl.
*G01N 33/24* (2006.01)
*G01N 3/42* (2006.01)
*G01N 33/36* (2006.01)

(52) U.S. Cl.
CPC .............. *G01N 33/24* (2013.01); *G01N 3/42* (2013.01); *G01N 33/36* (2013.01)

(58) Field of Classification Search
CPC ........... G01N 33/24; G01N 33/36; G01N 3/42
USPC ................ 73/866.86; 422/68.1; 435/4, 40.52
See application file for complete search history.

(56) References Cited

PUBLICATIONS

Gunasekhar Nachimuthu, Comparison of methods for measuring soil microbial activity using cotton strips and a respirometer, Feb. 21, 2007, Journal of Microbiological Methods 69 (2007) 322-329.*

(Continued)

*Primary Examiner* — Randy Gibson
*Assistant Examiner* — Gedeon M Kidanu
(74) *Attorney, Agent, or Firm* — Workman Nydegger (57) ABSTRACT

A method and a device for assessing the level of microbial activity of a substrate (9), preferably agricultural soil, biomass and other contexts, where there is enzymatic activity. The method includes: preparing one or more biodegradable threads (8); tensioning the one or more biodegradable threads with a pre-defined tension; introducing the one or more tensioned biodegradable threads partially in the substrate; leaving the one or more biodegradable threads in the substrate; measuring the time elapsed from the introduction of the one or more biodegradable threads in the substrate to the breakage of the one or more threads. The device includes one or more biodegradable threads (8) with a first fixing element (12) suited to fix one end of the biodegradable thread and a second fixing element (20) suited to fix the other end of the biodegradable thread, between which each biodegradable thread can be independently tightened with a pre-defined tension.

15 Claims, 8 Drawing Sheets

(56) References Cited

PUBLICATIONS

Stacy Harvey Brown, Woven Placemats, Jun. 19, 2009 (Jun. 19, 2009), XP055014545, Retrieved from the Internet:URL:http://www.thetextiledirectory.com/adm in/images/weavingwithoutaloom.pdf [retrieved on Dec. 12, 2011] figures Step 1-Step 3.*

International Search Report and Written Opinion dated Aug. 21, 2012, issued in PCT Application No. PCT/IB2012/001157, filed Jun. 13, 2012.

Gunasekhar Nachimuthu et al., *Comparison of Methods for Measuring Soil Microbial Activity Using Cotton strips and a Respirometer*, Journal of Microbiological Methods, vol. 69, 2007, pp. 322-329.

Stacey Harvey Brown, *Woven Placemats*, Jun. 19, 2009, XP055014545, pp. 3.

Raymond L. Correll et al., *Statistical analysis of Reduction in Tensile Strength of Cotton Strips and a Measure of Soil Microbial Activity*, Journal of Microbiological Methods, vol. 31, 1997, pp. 9-17.

P.M. Latter et al., *The Cotton Strip Assay for Cellulose Decompostion Studies in Soil: History of the Assay and Development*, ITE Symposium, 24, 1988, pp. 7-10.

J. P. Obbard et al., *The Use of the Cotton-Strip Assay to Assess Cellulose Decomposition in Heavy Metal-Contaminated Sewage Sludge-Amended Soils*, Environmental Pollution, vol. 81, 1993, pp. 173-178.

\* cited by examiner

METHOD AND DEVICE FOR ASSESSING THE LEVEL OF MICROBIAL ACTIVITY OF SOIL

TECHNICAL BACKGROUND OF THE INVENTION

The invention concerns a method, a device and a related kit for assessing the level of microbial activity of a substrate, for example cultivated soil, biomass and other environments where there is an enzymatic activity, based on the biodegradation of a material that allows the detection of the same. Various applications of the method and the device are described. An important sector for application is agriculture.

STATE OF THE ART

Several application sectors need answers to questions regarding the state of biological activity of a substrate. The soil, for example, which is the primary interface of agricultural production, constitutes an environment whose functionality is mediated by the activity of many microbial species. These determine the turnover of the organic substance and the nutrients destined for plant growth. The enzymatic activities of the soil are important "sensors", as they provide information on the metabolic condition of the microbial population and the chemical-physical conditions of the soil.

It is a need for the farmer to know the degree of fertility of its land and to assess whether it is necessary or not to supply, for example, nitrogenous and/or phosphatic fertilizers. The possibility to save money during said procedure, avoiding superfluous additions to the substances already available in the soil, would allow not only an economic benefit for the farmer but also a general advantage for the environment and the territory, as shown by the severity of the problems related to the excess of nitrates of agricultural origin in water beds and running water and by the consequent measures provided for by the law.

In addition to current cultivations, the knowledge of the productive potential status is required for land at rest in order to determine the optimal shifts and durations for restarting cultivation or valuating the opportunity to reconvert marginal lands for cultivation.

In the same way, the knowledge of the maturation state and of the activity of a substrate is required even in the case of the maturation of manure or fowl dung, of the composting of organic residues, of biopiles of soil dedicated to bioreclamation, as well as in a series of industrial situations whose fulcrum is the activity of microbial consortia in tanks or bioreactors. Among them it is possible to mention activated muds, waste water treatment, nitrification-denitrification systems and the conversion of biomasses and agro-industrial residues for the production of biogases and biofuels.

The present methods through which it is possible to meet the needs of the involved users (farmers, plant managers, environment protection agencies, legislators) regarding the knowledge of the microbiological condition of soils, environments, bioreactors, etc consist of a series of chemical-physical analyses having one or more of the following disadvantages: the need to entrust specialized laboratories with the task; the need to analyse many distinct aspects (element dosage, chemical-physical analyses, microbiological analyses); the difficulty in interpreting the results for the purposes of a univocal diagnosis; the medium-high costs of the analyses; the long waiting times depending on the availability of the analysis service; the need to have the material transported out of the involved site to the analysis site.

The known art provides a method that analyses the degree of degradation of samples of a textile fibre (cotton) by placing them in the soil and taking them out after a pre-defined period of time to measure their residual mechanical resistance after interaction with the micro-organisms. The force necessary for breakage is an indicator of the cellulolytic activity of the soil. According to the method, the sample is transported to analysis centres. The use of large strips requires long periods in the ground and large tensiometric machinery to break them. The method does not provide any information regarding other enzymatic activities, for example proteolytic activities, or information on the contents of nitrogen, phosphorous, potassium etc in the ground.

Many authors have described the known method used to analyse soils, for example the following: Nachimuthu et al. in "*Comparison of methods for measuring soil microbial activity using cotton strips and a respirometer*", Journal of Microbiological Methods, Elsevier, Amsterdam, NL, vol. 69, no. 2, 13 Apr. 2007, p. 322-329; Raymond L. Correll et al. in "*Statistical analysis of reduction in tensile strength of cotton strips as a measure of soil microbial activity*", Journal of Microbiological Methods, vol. 31, no. 1-2, 1 Dec. 1997, p. 9-17; P. M. Latter et al. in "*The cotton strip assay for cellulose decomposition studies in soil: history of the assay and development*" in "*Cotton strip assay: an index of decomposition in soils*," Grange-over-Sands, NERC/ITE, 7-10. (ITE Symposium, 24), 1 Jan. 1988; and J. P. Obbard et al. in "*The use of the cotton-strip assay to assess cellulose decomposition in heavy metal-contaminated sewage sludge-amended soils*", Environmental Pollution, vol. 81, no. 2, 1 Jan. 1993, p. 173-178.

DESCRIPTION OF THE INVENTION

It is the object of the present invention to overcome the disadvantages described above and in particular to provide a method and a device capable of facilitating the assessment of the microbial activity of a substrate, in particular of a soil, with no need to transport samples to analysis centres, to use complex measuring instruments, to bear high costs and wait for long times. It is a further object of the invention to provide a method and a device capable of supplying in a simple manner, with no need to perform many different analyses, global information on the microbial activity of the substrate, including several enzymatic activities and optionally of obtaining also information on the availability of fertilizer/nutrient elements like nitrogen, phosphorous, potassium etc. in the substrate. It is also the object of the invention to find other fields of application for the method and the device of the invention in addition to the application in the field of agriculture.

The objects mentioned above and other that will be highlighted in greater detail below are achieved by a method for assessing the level of microbial activity of a substrate, preferably soil, comprising the following steps:
a) preparing one or more biodegradable threads;
b) tensioning the one or more biodegradable threads with a pre-defined tension;
c) at least partially introducing the one or more tensioned biodegradable threads in the substrate;
d) leaving the one or more tensioned biodegradable threads in the substrate; and e) measuring the time elapsed from the introduction of the one or more tensioned biodegradable threads in the substrate until the breakage of the one or more tensioned biodegradable threads.

The tests performed have shown that in the threads recovered after they were introduced in the substrate it is possible to record a precise variation in the resistance to the dynamometric breaking stress compared to the original threads not introduced in the substrate, and that this parameter is highly related to the levels of microbial activity of the environments being analysed. The microbial/enzymatic activity is determined by the presence of organic substance and the availability of nutrients in the substrate being examined. The level of microbial activity is an indicator of the state of maturation and/or fertility of soil or another substrate.

The term "thread" means an elongated body whose longitudinal dimension (length) exceeds its cross dimensions (width and thickness). Correspondingly, the term "thread" comprises also fibres, and a thread may be comprised of a plurality of fibres or one fibre only. The term "fibre" includes single filaments, multiple filaments, fibre tufts, strips or bands or fibres cut in other shapes, broken in small pieces or discontinuous or the like, with regular or irregular cross sections and suited to be subjected to a given tensile stress. The term "fibres" herein comprises also combinations of the structures mentioned above.

The term "biodegradable" means that the thread/threads is/are at least partially biodegradable. In other words, it is sufficient that the degree of biodegradability, meaning the ability of the thread to be decomposed by a microbial flora, whose presence must be determined adopting the method according to the invention, be such that a given microbial activity in the substrate in question may cause the breakage of the thread/threads being tensioned within a certain period of time. Preferably, this period of time should not exceed 1-2 weeks.

In the case where the substrate is soil, suitable threads could for example be compostable threads. All the materials can be considered suitable which are sufficiently biodegradable and able to support a certain tension. Materials of natural origin but also artificial materials, like polymeric fibres, can be taken in consideration. Natural materials are divided in materials of animal origin, generally made up of proteins, and materials of vegetable origin, generally made up of cellulose or starch-based.

According to a preferred variant embodiment of the invention, the biodegradable threads are of proteinaceous or vegetable origin, preferably cotton or silk. The degree of decomposition of the threads supplies information on the cellulolytic or proteolytic activity of the substrate. The choice of the material, among other things, is also determined by the speed with which the micro-organisms or the enzymes are capable of decomposing the thread in order to cause the breakage of the same. Ideally, the threads, their tension and their sizes are selected in such a way that the breakage of the threads takes place within a few days, maximum within 1-2 weeks.

Compared to the state of the art, the method of the invention does not measure the traction force necessary to break the thread after a given period of time but the time elapsed until the breakage of the thread subjected to a given tensile/tractive stress, which considerably simplifies the measuring technique. The stay of the thread in the soil allows the micro-organisms/enzymes to decompose the biodegradable material with the consequence that after the decomposition of a given quantity of material the thread cannot bear the tension any longer and breaks. Cotton or silk sewing threads available on the market have shown to be particularly suitable for the intended purpose. This method, according to which threads are laid into the ground (or immersed, in the case of more liquid substrates like muds) has been developed in order to measure the degradation capacity of the complex of micro-organisms present in soils and substrates. Preferably, at least two of the one or more biodegradable threads are made of different materials in order to gather information on different microbial activities.

Advantageously, the threads are of vegetable origin (for example, cellulosic, like cotton) or of animal origin (for example, proteinaceous, like silk). The thread of vegetable origin is susceptible of a cellulolytic action while the thread of animal origin is an indicator of proteolytic activity. They are gradually weakened by the progressive activity of the free micro-organisms or enzymes with which they are in contact. In the application of the method, combining threads in different materials means obtaining, from the time necessary to break them, information on the proteolytic activity and the cellulolytic activity of the soil. Other types of thread can be taken in consideration, like for example linen, viscose, wool (which has shown to degrade slowly) etc.

In an advantageous embodiment of the method of the invention, for at least one of the one or more biodegradable threads there is at least one further biodegradable thread in the same material with the addition of at least one fertilizing substance and the lack or excess of the fertilizing substance in the substrate is determined through the comparison of the breaking time of these two threads. This variant embodiment of the method is particularly interesting in the field of agriculture and makes it also possible to determine whether the fertility of the soil in question can be further increased.

Besides the simple fibres described above, other versions are thus added and placed in the substrate, to which sources of fertilizing elements, like for example mineral nitrogen or potassium phosphate, are previously added. In this context it is possible to take in consideration different combinations of threads, each containing a fertilizing element, or of threads having several fertilizing elements. Of particular interest are the fertilizing substances selected from the group constituted by mineral sources of nitrogen, phosphorus, potassium, calcium, magnesium, sulphur and other meso and microelements. These elements can be found in mineral salts like $Ca(H_2PO_4)_2$, $CaSO_4$, $CaNaPO_4.CaSiO_4$, $(NH_4)_2HPO_4$, $NH_4NO_3$, $(NH_4)_2SO_4$, $KNO_3$ and others known to the expert in the field.

In the sectors of agriculture and gardening, the meso elements are considered secondary elements based on the plants' answer to specific additions made through fertilization. The meso elements include for example calcium, magnesium, sulphur, chlorine and in some cases also sodium is considered. The macro elements, instead, are the main elements for fertility, in particular nitrogen, phosphorus and potassium. The micro elements, instead, act in very limited quantities but carry out a fundamental role, since they are part of the components of enzymes. They include, for example, boron, manganese, copper, zinc, molybdenum, cobalt, iron and sometimes also chlorine, silicon and nickel are mentioned as belonging to this group.

In the simplest case, the enrichment with nitrogen takes place through the immersion of the threads in a $NH_4NO_3$ solution. Preferably, the concentration of the solution is approximately 3 g/l. Preferably, the immersion time is approximately 15 min.

To advantage, the enrichment with phosphorus requires, instead, immersion in a $Na_2HPO_4$ and $KH_2PO_4$ solution. A suitable concentration is approximately 6 g/l of $Na_2HPO_4$ and 3 g/l of $KH_2PO_4$. Advantageously, the threads are then dried in the open air.

In the cases where weakening of the resistance to breaking in the thread pretreated with a particular element is even greater than in the non-pretreated thread, said difference indicates in what measure fertilization with the respective element can be of benefit to the soil in question. It is thus easy to obtain information on demand in relation to this specific element tested.

The differences in fact indicate if and how much, in the soils in question, the micro-organisms active in the mineralization of the organic substance are limited by this element, for example nitrogen or phosphorus.

In conditions of excess nutrients in the soil, pre-treatment with a given element has shown to be suitable for indicating the result, even if negative, causing minor degradations compared to the fibres to which this element has not been added.

This is particularly evident in the case of nitrogen.

In other words, the farmer can understand autonomously, using the proposed method with several threads, whether his soil needs the addition of certain elements, like phosphorus or nitrogen, or not.

The method has been validated by several thousand measurements made on soils and contexts with known fertility and productivity and the correlations with the required parameters were highly significant.

To express the result, the resistance value of the threads placed in the soil is compared with the average resistance value of corresponding native threads that were not placed in the soil and expressed as a resistance percentage with the following formula: (grams of applied weight necessary to break the fibre placed underground/grams of applied weight necessary to break the native fibre)×100. The data obtained have then been converted from residual resistance percentage to percentage of degradation occurred, subtracting the resulting value from 100.

The correlation of the values determined in this way with certain concentrations of bacteria, microfungi, algae, protozoa, enzymes or fertilizing elements in the substrate takes place through a "setting" with substrates whose chemical-physical and microbiological parameters, like for example information on the type of soil, the concentration of nutrient/fertilizer elements, the quantification of the microbial population, values regarding the enzymatic activity etc. are known.

Obviously, it is possible to transfer this part of the method (placing underground threads in different materials and/or threads in the same material, pretreated and non-pretreated) also to the method of the known art, then to the method for measuring the force necessary to break the threads after a given period of permanence in the soil.

The invention thus achieves the object to provide a method for the comparative assessment of the level of microbial activity and/or the state of fertility of soils or of the aptitude to degradation of muds and waste waters containing biologically active communities, as a function of the microbial mineralizing activity of the organic substance on biodegradable sample threads (for example cotton, silk), placed in the soil or immersed, both in the simple form and with the addition of fertilizing or nutrient elements (for example nitrogen, phosphorus and potassium), through the measurement of the variation in the resistance to breaking after a suitable period of permanence in the soil or in the substrate being analysed.

The method according to the invention makes it also possible, for example, to monitor the reclamation of soils that have become polluted following phytoextractions or pollution in general. The method allows different activities to be simultaneously determined.

Another aspect of the present invention concerns a device for measuring the level of microbial activity of a substrate, comprising one or more biodegradable threads and for each biodegradable thread a first fixing element suited to fix one end of the biodegradable thread and a second fixing element suited to fix the other end of the biodegradable thread, between which each biodegradable thread can be independently tightened with a pre-defined tension. Obviously, at least the first fixing element can be common to two or more threads, and in the same way each thread may have from time to time a single first fixing element. This device is suited to implement said method. For the terms to "thread" and "biodegradable" the definitions provided above apply.

The device according to the invention is preferably a measuring device for the soil.

According to a preferred variant embodiment of the invention, for at least one biodegradable thread there is at least another biodegradable thread made of an identical material provided with at least one fertilizing substance and/or there are at least two biodegradable threads made of different materials. Respective variants and combinations have been described above regarding the method according to the invention. By placing in the ground a single device it is possible to introduce in the soil various combinations of multiple fibres, integrated in a single probe.

In the simplest form there are a first and a second fixing element for each biodegradable thread present.

It is possible to consider the production of the pre-defined tension on the thread by setting in advance a given distance between the two fixing elements, but advantageously the device also comprises a tensioning element suited to exert a given traction force on the biodegradable thread to obtain the pre-defined tension on the thread. Such a tensioning element can for example be a spring. Ideally, the threads are subjected, through these tensioning means, to a traction force equal to 50% of the traction force necessary to break the same filaments when they are new. In this regard the market offers springs set with pre-defined elastic forces suited to exert specific traction forces on the thread. Preferably, the tensioning means control the distance between the first and the second fixing element.

Preferably, the device according to the invention also comprises, for each biodegradable thread, an indicator suited to signal the breakage of the same thread. The presence of an indicator avoids the need to extract the device from the substrate at determined intervals to control the conditions of the thread and makes it possible to leave the instrument in situ in the ground and record the time necessary for the indicator to be activated following the breakage of the specific thread, once its resistance has lowered, for example, to half the resistance of the native fibre.

According to an advantageous variant embodiment of the invention, the second fixing element can be moved with respect to the first fixing element and the tensioning element is a spring that exerts its traction force on the second fixing element so that a biodegradable thread tightened between the two fixing elements loads the spring that, in case of breakage of the thread, moves the second fixing element away from the first fixing element returning to its unloaded position. Two main cases can be taken in consideration. In the first case the spring, when the thread is tensioned, is extended from its unloaded rest configuration, while in the second case the spring is compressed when the thread is tensioned. Once the thread has broken, the spring respectively contracts or expands, returning to its unloaded configuration.

Preferably, the indicator is integral with the second fixing element and thus moves with it, and consequently its position is suited to signal the breakage of the thread, if this occurs. Since it is the spring that exerts the traction force on the second fixing element and this fixing element is movable, the position of the second fixing element is determined by the extended or compressed condition of the spring that in turn is determined by whether the thread is tensioned or not. An indicator directly connected to the second fixing element is capable of indicating, as a position indicator, the position of the second fixing element and thus, indirectly, the condition of the thread, which may still be tensioned or may have broken. The construction concept includes, in the simplest case, the possibility of a direct visual monitoring of the indicator that for this purpose, to advantage, should be positioned in a portion of the device that is not placed in the soil.

Preferably, the indicator moves from one position to another and thus comes into contact with a detector that shows the condition of the thread on a display or remotely; this principle can also be changed with simple adjustments, obtaining a variant capable of providing the detected condition by means of wireless transmission of data to a suitable software. In this way the instrument is capable of automatically returning the information that is useful for consequent management choices of the user, such as: whether there is or not the need for land fertilization and entity of the same in cultivated soils; quality, potential and vocation of uncultivated and woodland soil; suitability of the soil for re-cultivation after being left fallow or as set-aside; degree of maturation/activity of heaps of manure, composting masses, biopiles for land reclamation, sediments resulting from both natural and artificial contexts, muds and systems for treating biomasses and waste waters, and bioreactors in the energy production chain etc. This information can be supplied from the corresponding to combination of different threads, as described above.

Advantageously, between the two fixing points of the thread there is a thread guide suited to slightly incline the thread with respect to the main axis of the instrument, preferably defining an inclination of around 3° if the thread is approximately 15 cm underground. In a possible variant embodiment, the thread guide is disc-shaped and provided with recesses arranged radially, wherein these recesses can be simple slits or recesses in a star-shaped disc. According to an advantageous embodiment of the device, the base structure of said device is a bar that for each biodegradable thread is provided in its lower part with said first fixing element and, axially spaced from this first fixing element, with a separating element housing for each thread, in an axially moving configuration, a rod whose first end, which is on the side of the separating element facing towards the first fixing element, is provided with said second fixing element and along whose length, on the other side of the separating element, there is a spacer integral with said rod, and wherein said spring is coaxially inserted in said rod so as to be enclosed between said spacer and said separating element, in such a way that by fixing said thread between said first and said second fixing element, the thread is tensioned and the spring is compressed between the spacer and the separating element, and in case of breakage of the thread the spring extends, thus moving the rod whose second end is said indicator that by moving together with the rod signals the breakage of the thread through its new position.

The dimensions of the device according to the invention are variable and depend also on the substrate to be analysed. The device for application in vases, for example for ornamental plants, will be smaller than the version for use in fields, vineyards, orchards, ornamental gardens or natural environments. The length of the thread portion in contact with the soil is selected according to the extension of the in-depth microbial activity of the substrate. The density of the instruments, that is, the number of instruments for a specific surface being analysed, depends on the homogeneity of the substrate, which is generally higher in the case of plains than in the case of hills. Indicatively, on a plain an average of six monitoring points per hectare of ground may be sufficient. The diameter of the thread is optimized based on the desired time of permanence in the ground.

Advantageously, the device can also be equipped with analysers selected to among gas, temperature and humidity analysers in order to complete the information collected.

A further aspect of the invention concerns a kit comprising one or more biodegradable threads as well as a) biodegradable threads pretreated with solutions of mineral salts containing at least one mineral source selected among sources of nitrogen, phosphorus, potassium, calcium, magnesium, sulphur, other meso and microelements; and/or b) solutions of mineral salts containing at least one mineral source selected among sources of nitrogen, phosphorus, potassium, calcium, magnesium, sulphur, other meso and microelements, in which the ends of the threads are provided with fixing means, in particular spherules, eyelets, hooks, and are optionally provided with a distinctive mark. These fixing means are advantageously selected so that they are suited to be fixed with fixing elements present in a measuring device according to the invention. Such a kit serves to easily replace the broken threads with threads that may serve for the measurements to be carried out.

For the terms "thread" and "biodegradable" the definitions provided above apply. A distinctive mark can be a coloured spherule.

The advantages offered by the method and the instrument proposed compared to the existing technology are evident, as they offer the user: the opportunity to use the instrument on his land, in his factory, plant or garden or vase; the possibility to make the diagnosis by himself by comparing the times determined for the breakage with times known for substrates with known qualities (for example, listed in apposite interpretation tables); the opportunity to obtain answers in real time or in any case very shortly; and the opportunity to use an instrument that has a low price and can be re-used indefinitely by replacing the changeable fibres only. The determination of the properties of the substrate can allow the users to take direct and timely decisions regarding the possibility to add fertilizers only when this is actually necessary and to use the most suitable type of fertilizer, thus performing a "precision fertilization", and regarding the opportunity to use materials that have reached maturation (compost, dung) instead of waiting for unnecessary or even excessive periods with respect to the functionality of the product. These choices allow the user to save considerable amounts of money and reduce waste and the diffusion of to excessive quantities of fertilizers in the environment, in addition to reducing the waiting times for interventions and the marketing/distribution of the products. Using the method and the device according to the invention it is no more necessary to recover the threads and measure their residual ultimate tensile stress on a dynamometric bench, as the device can operate automatically and is only the measurement of the time of exposure to micro-organisms necessary to break the threads is needed. In this way, the monitoring of the microbial (mineralizing) activity and/or of the fertility of the soil, which is closely related to it, can be comfortably carried out by periodically checking the condition of the indicators provided on the instrument (or receiving the data from wireless sensors in the remote detection version) and comparing the determined values with standard values supplied, for example, in interpretation tables.

The invention achieves the object to allow a comparative analysis (between different biodegradable materials and/or threads with or without addition of nutrient elements, in particular: nitrogen or phosphorus-potassium) which constitutes a considerable methodology improvement providing information not only on the cellulolytic activity but also on the proteolytic activity and/or on the concentrations of nutrients (fertilizing elements) that may already be present or residual in the soil or even absent. Furthermore, the use of considerably thick strips instead of thin threads in the known art requires large tensiometric machinery used in the textile industry and long stays underground to break such strips. The method and device of the invention do not require sophisticated tensiometric instruments; the stays underground are shorter. The present invention is not limited only to the application to soil, in fact the method and the device can be used also in other contexts as described above, for example also in the paragraph regarding the state of the art. The invention provides an instrument (optionally automatic) for assessing the level of microbial activity and fertility of a substrate that can be monitored by the user. If the device and/or method is applied to substrates with known microbial/enzymatic activities, they may be useful to determine the biodegradability/compostability of materials, for example polymeric materials. For this purpose, threads made of the material to be tested are used.

Variant embodiments of the invention are the subject of the dependent claims. The description of a preferred example of embodiment of the device according to the invention is provided by way of non-limiting example with reference to the attached drawings.

DESCRIPTION OF THE EXAMPLES OF EMBODIMENT

Figure 1:
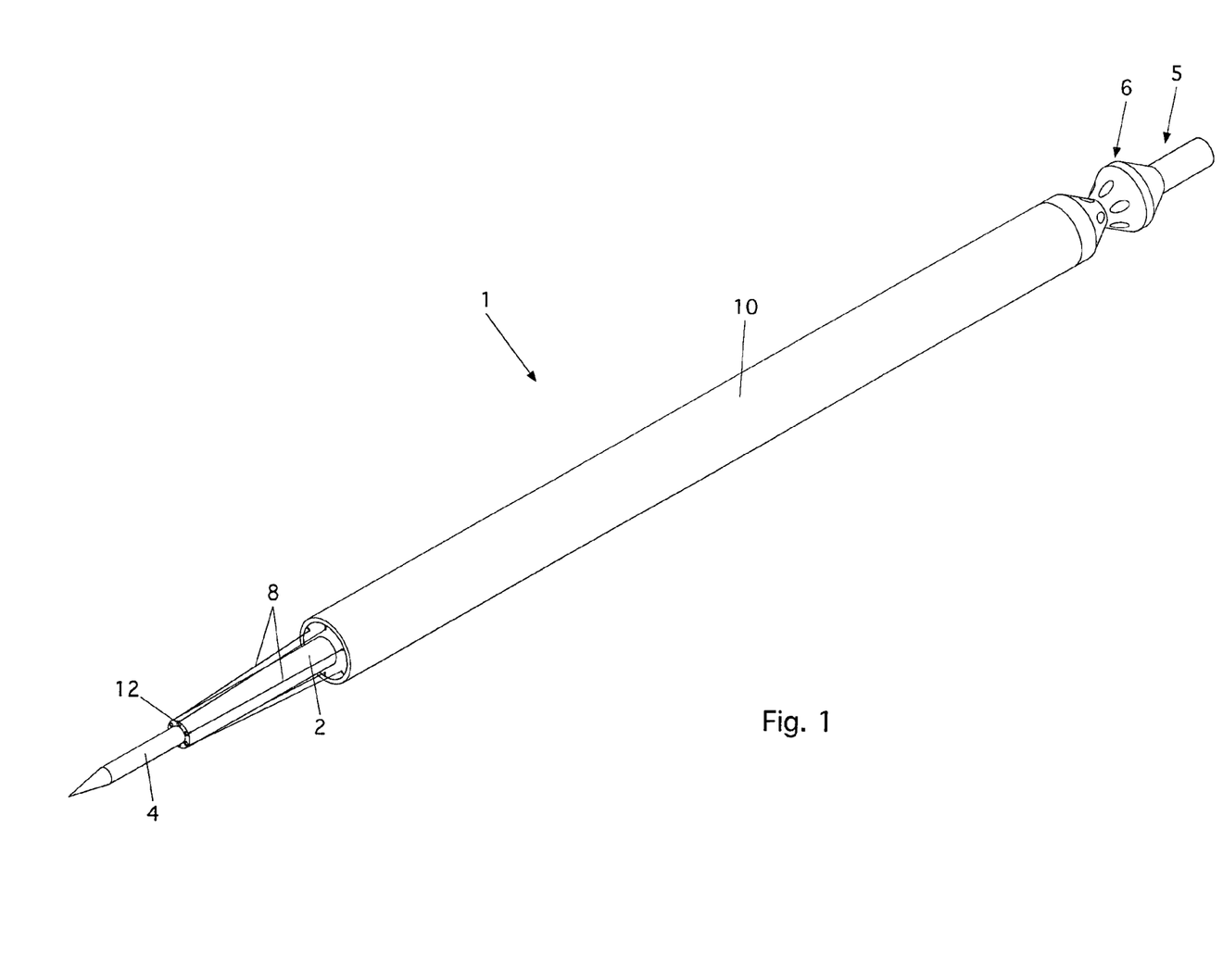
FIG. 1 shows an axonometric view of a device for assessing the level of microbial activity of a substrate according to the invention.

FIG. 1 shows a device in the version for use in fields, indicated as a whole by 1. The base structure comprises a bar 2 provided with a stabilizer tip 4 at one end. On the opposite end 5 that also serves as a grip there is a measuring head 6 capable of measuring the activation of an indicator (not shown) that signals the breakage of one of the biodegradable threads 8. Since the device 1 is intended to be used mainly outdoors, the tensioning mechanisms (illustrated in detail in the following figures) will be protected against the weather agents by means of a cylindrical casing 10 whose upper portion is transparent, so as to allow the coloured indicators (see FIG. 6) that may be activated to be seen. Said casing 10 has a simple design and can be easily removed through an axial sliding movement in order to allow the rapid positioning of new threads, available as spare parts, with no need for special tools. Fixing elements suited to fix from time to time one end of corresponding biodegradable threads 8 are indicated by 12.

Figure 3:
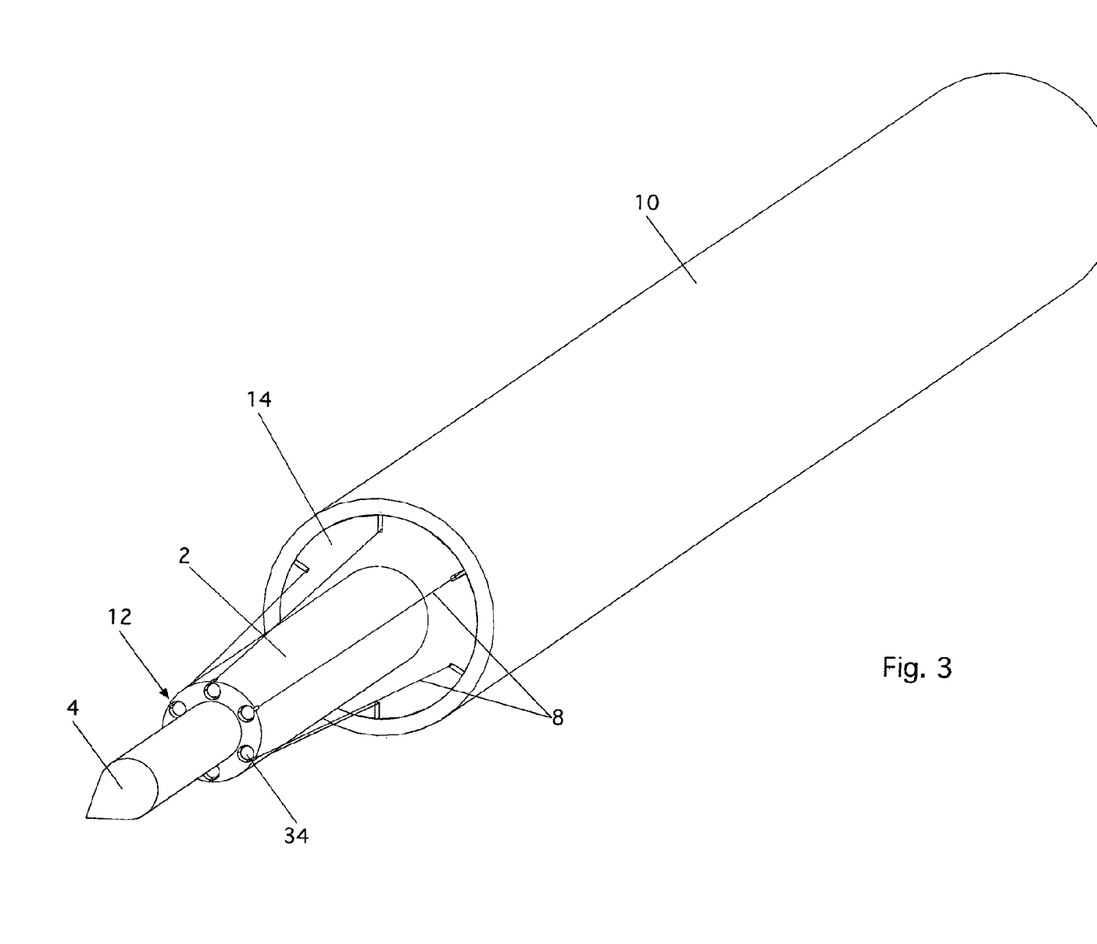
FIG. 3 shows an axonometric view of the lower part of the device according to FIG. 1.

In the example shown in FIG. 3 the threads are anchored at the bottom by means of coloured spherules 34, fixed through a standard industrial process, serving as stoppers and inserted in the apposite cylindrical elements 12 to present in the lower part of the instrument, above the stabilizer tip 4. The bar 2 is made of a material suitable for use in fields, like for example stainless steel, polymeric materials etc. The stabilizer tip 4 should ideally be introduced in a pre-hole made in the ground using a punch with suitable diameter, preferably slightly smaller than the diameter of the bar 2 in order to guarantee good contact between the threads 8 and the soil. In the case of soils that are not too hard it is also possible to insert the device directly, with no need to make a pre-hole and without risk of breaking the threads.

Figure 2:
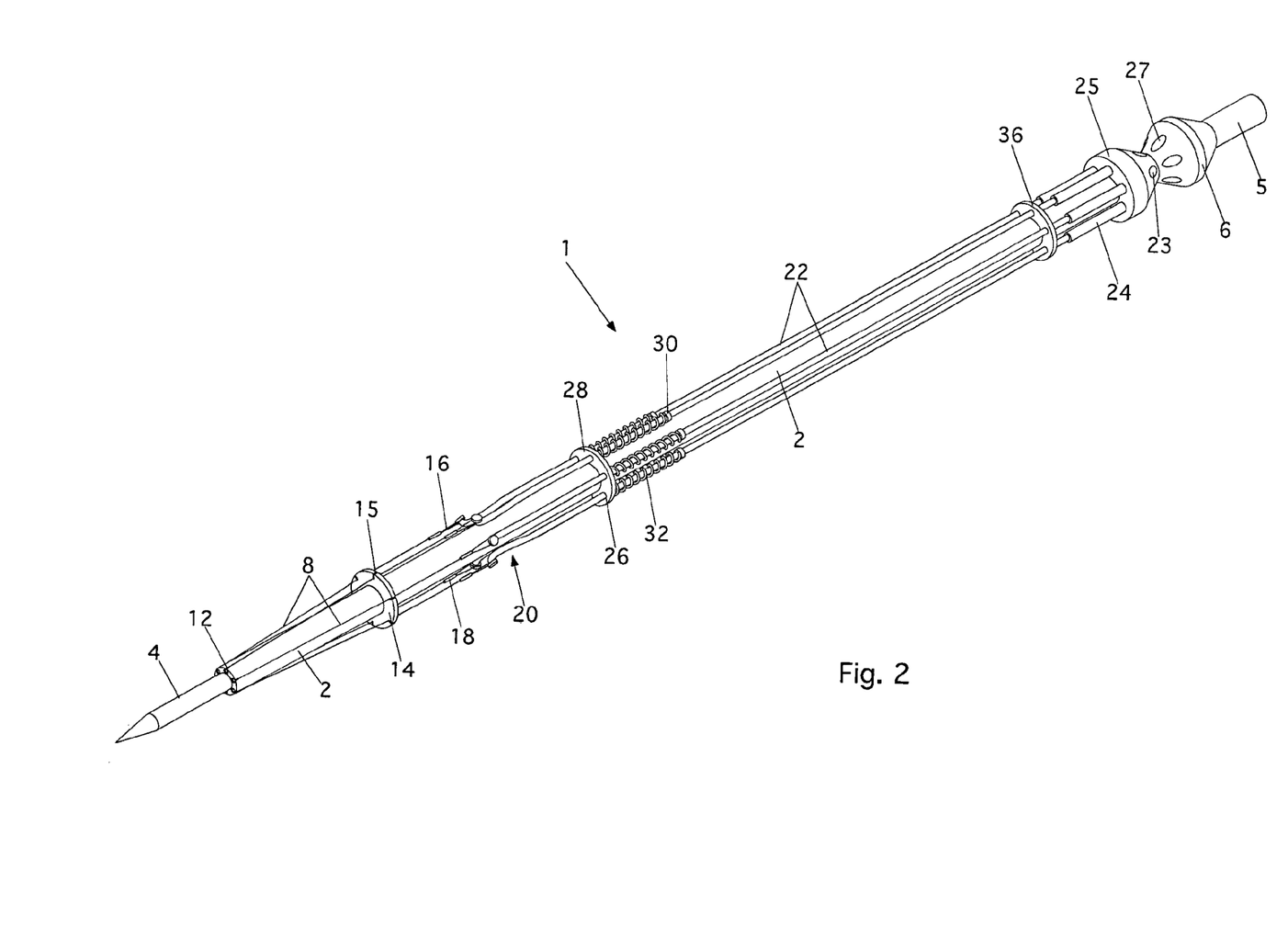
FIG. 2 shows an axonometric view of the device according to FIG. 1 without the protection casing.

FIG. 2 shows the inside of the device 1 after removal of the protective casing 10. The biodegradable threads 8 extend from the respective fixing elements 12 along the bar 2 and are guided through a disc-shaped thread guide 14 that besides spacing the threads 8 from each other also serves to define a specific inclination of the threads 8, each one of which ends with an eyelet 16. This is obtained, for example, by preparing the upper end of the threads 8 in the shape of an eyelet with small coloured plastic cylinders 18 that are hot formed around the threads through a standard industrial process used in the textile and in the clothing industry. These small coloured cylinders 18 are also useful to distinguish the threads from one another according to the material used and the different substances added. The resulting divergence of the threads 8 ensures contact with the soil and therefore the best interaction with the micro-organisms.

An inclination of approximately 3° has shown to be suitable for a length of approximately 15 cm of contact between soil and threads constituting the active substrate. The eyelets 16 are coupled with hooks 20 that correspond to the first end of rods 22 extending along the bar 2 and ending in second coloured indicator ends 24. These indicators 24 are gathered in holes 23 of a head 25. The rods are movably guided in holes 26 of a disc 28 and are provided with fixed rings 30. The rings 30 and the disc 28 limit the mobility of helical springs 32 (just one spring has been represented for the sake of clarity) inserted in the rods 22 between the rings 30 and the disc 28. The springs develop a given elastic reaction so as to apply a specific tensile force to the thread 8. The threads 8 are thus maintained tensioned on the vertical line by the rods 22 loaded by these helical springs 32.

In the example described herein there are six threads (three cotton threads and three silk threads) and each group comprises: (a) one non-pretreated to control thread, (b) one thread pretreated with nitrogen and (c) one thread pretreated with phosphorus. Obviously, the final user is free to choose also other combinations of thread materials and thread treatments to obtain the desired information. Obviously, also the number of threads may vary. The threads are ideally produced industrially with standard characteristics and advantageously provided with spherules and small cylinders in specific colours in order to allow correct insertion in the device. This is necessary as the traction force used for cotton is different from the traction force used for silk and, with the same material, it will be necessary to be able to distinguish among the various threads, cotton or silk, neutral or pre-treated, for a correct assessment of the results.

For this purpose even the upper indicator ends 24, which will be activated when the thread, once having reached a degree of degradation of 50%, will yield to the traction of the spring and break, are marked with a different colour in order to allow the correct insertion of the threads during assembly and the identification of the broken thread during examination of the results by the user. The locking system (spherules, eyelets) adopted makes it possible to position the threads 8 in the device 1 quickly and with no need for special tools.

After the insertion of the stopper spherule 34 in its seat (FIG. 3), each thread 8 is passed through a groove 15 provided in the thread guide disc 14, necessary to maintain a slight angle (~3°) between the thread 8 and the vertical axis of the bar 2, and finally secured to the lower end of the corresponding rod 22 provided with a hook 20. The threads 8 are thus slightly divergent from bottom to top, in order to achieve better contact with the substrate. In fact, the instrument is inserted in a pre-hole made with a simple tool consisting of a metal or plastic cylinder or punch, provided that its diameter is equal to or slightly smaller than the diameter of the portion of the device positioned in the soil and its length is equal to that of the portion of the device positioned in the soil, excluding the stabilizer tip, corresponding to the depth of the active layer (~15 cm). The device 1 is ideally provided with a second spacer disc 36 positioned on the upper part of the device to maintain the rods 22 essentially parallel to the rod 2.

Figure 8:
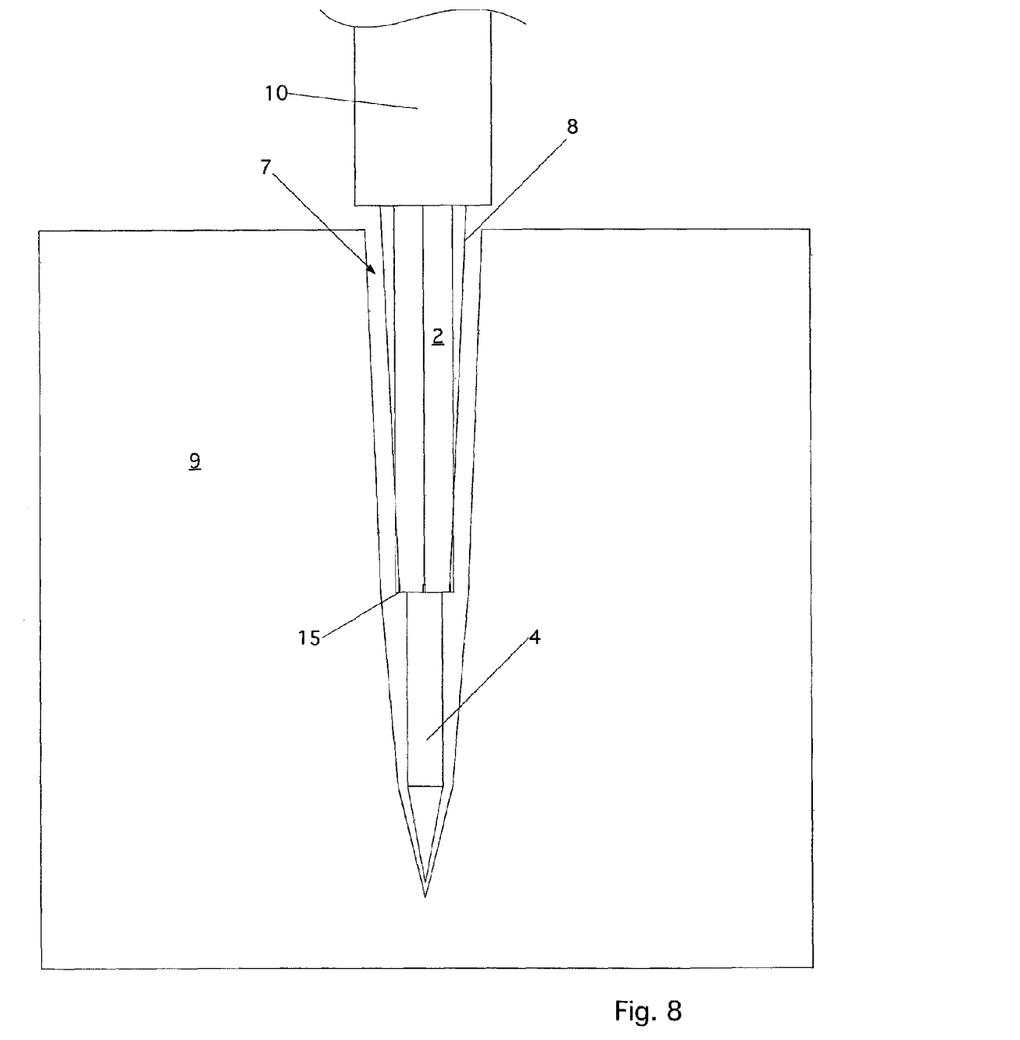
FIG. 8 shows a side view of the introduction into the soil of the lower part of the device according to FIG. 1.

FIG. 8 shows the positioning of the stabilizer tip 4 and of the threads 8 to a suitable depth into a hole 7 made in a soil 9. For clarity reasons, in the drawing to there is an empty space between the soil 9 and the threads 8; the soil actually occupies all the space and touches the bar 2. When the device is inserted in the hole 7, all the threads 8 maintain a uniform contact with the soil and with the external cylindrical surface of the bar 2, even in case of a slight inclination of the device with respect to the vertical line.

Figure 4:
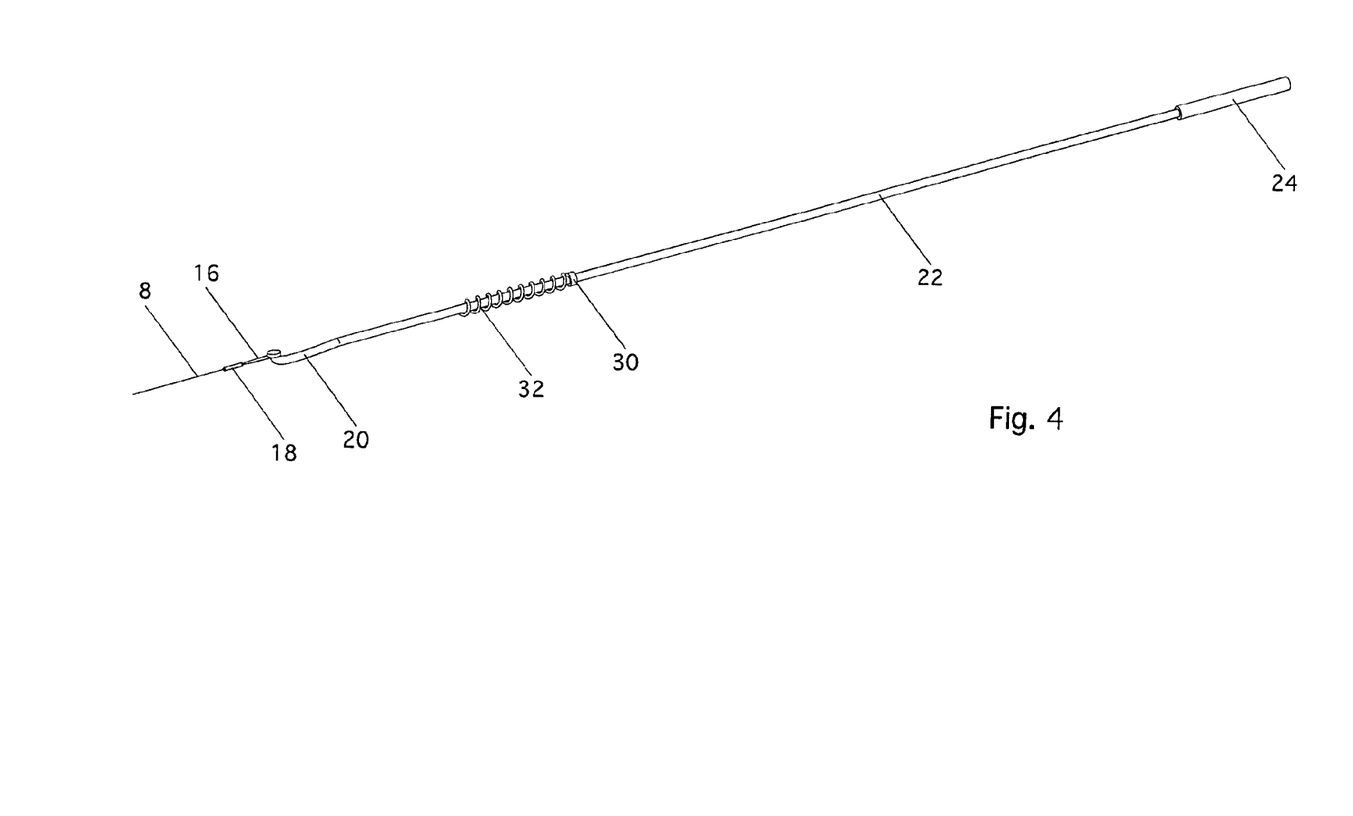
FIG. 4 shows an axonometric view of a detail of FIG. 2.
Figure 5:
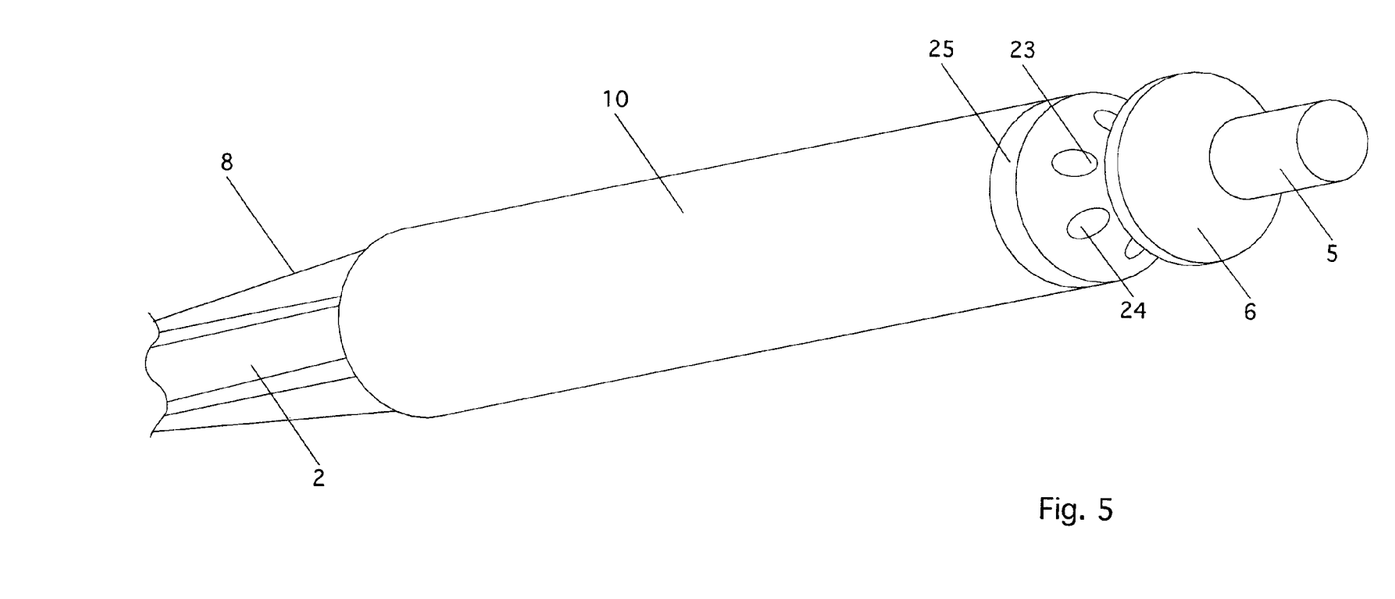
FIG. 5 shows an axonometric view of the head of the device according to FIG. 1 with indicators not activated.

FIG. 4 shows an enlarged view of a rod 22 of the device 1 with the indicator 24 and the hook 20. The spring 32 can be replaced by simply withdrawing it from the rod 22 which can be easily inserted in a hole 26 in the spacer disc 28. FIG. 5 shows the upper part of the instrument 1 with none of the indicators 24 activated but all withdrawn in the holes 23 of the head 25.

Figure 6:
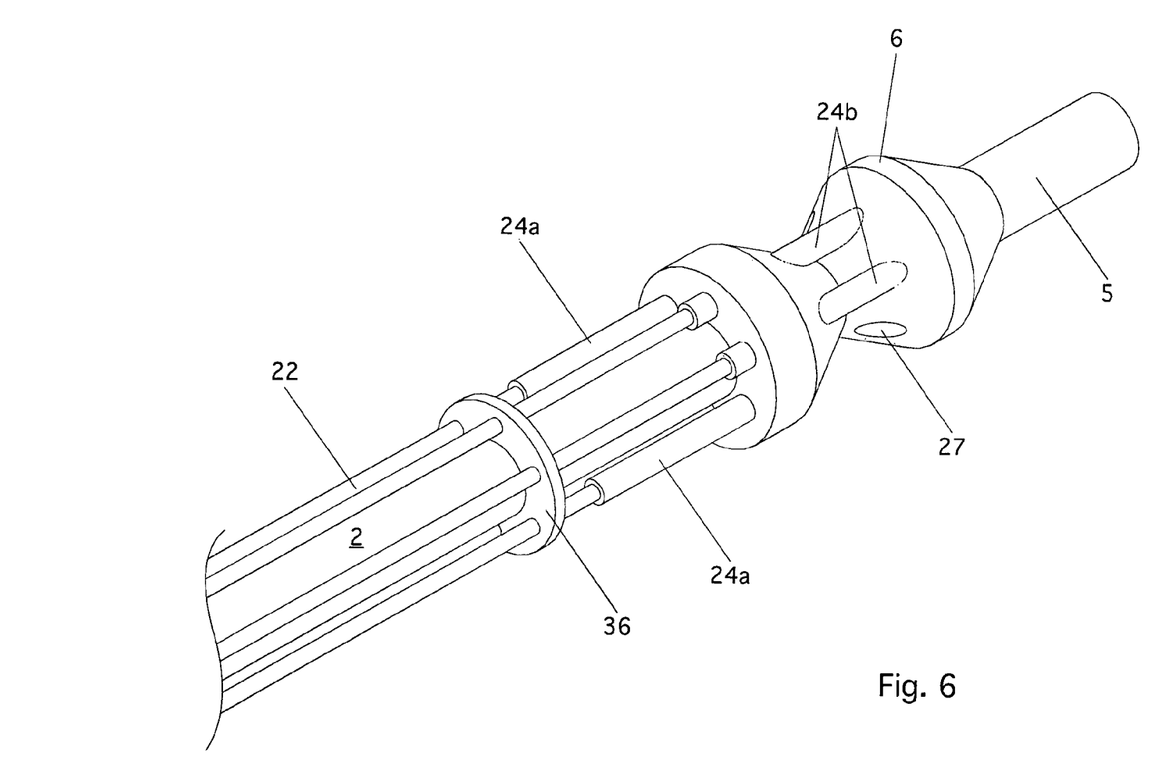
FIG. 6 shows an axonometric view of the head of the device according to FIG. 2 with some indicators activated.

FIG. 6, instead, shows two indicators 24b that are activated and visible even if covered by the protective casing, since due to the yielding of the respective threads their rods 22, no more held by the respective broken thread, have been pushed upwards by their spring. Some indicators 24a are not activated, meaning that the corresponding thread has not broken yet.

Around the indicators 24 there may be a transparent protective strip in a plastic material suitable for the context of use, not illustrated in the drawing, which may even be an integral part of the protective casing. The upper protections of the indicators, if any, have been omitted in all the drawings.

The upper head 6 is provided with holes 27 thus serving as a seat for the activated indicators 24 and can house an electronic circuit with microprocessor suited to detect their status, a miniaturized GPS receiver, a WSN module, a chronometer to measure when the indicator is activated and a power supply battery.

Figure 7:
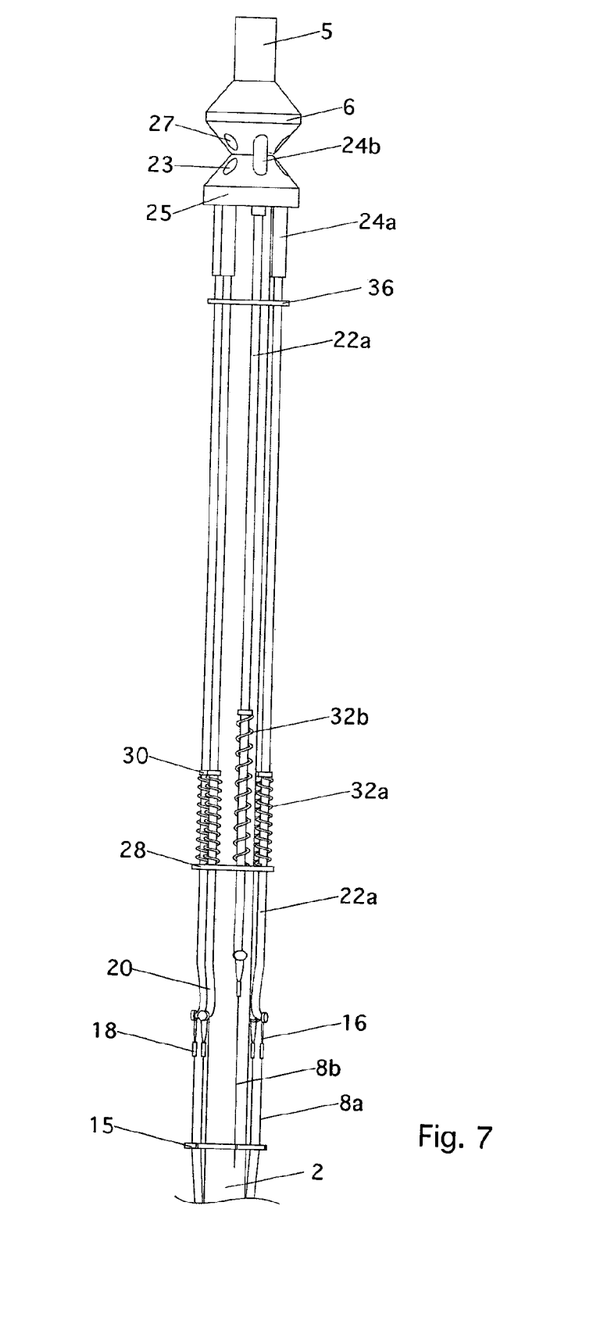
FIG. 7 shows a side view of the upper part of the device according to FIG. 2.

FIG. 7 sums up the different situations of the measuring system in a side view of the upper part of the device. The threads 8a are still tensioned, while the thread 8b is broken. Correspondingly, the rods 22a connected to the unbroken threads 8a are in a lower position compared to the rod 22b connected to the broken thread 8b. The threads 8a cause the compression of the corresponding springs 32a, while the breakage of the thread 8b has allowed the spring 32b to return to its unloaded configuration pushing the respective rod 22b upwards. The corresponding indicator 24b is axially displaced with respect to the indicators 24a that have not been activated and signals the breakage of the thread 8b.

The device can be used in a context with remote detection option. The structure of the instrument allows the insertion, in the upper part, of an optional module with wireless technology, complete with a battery with suitable capacity, for the remote transmission of the status of the various indicators.

The actual technology of the WSN (Wireless Sensor Network) networks makes it possible to create a network of interconnected sensors, as already is happening in the industrial field, for the detection of the condition of said sensors and the transmission of the process parameters with no need to provide a specific wiring.

By adopting this technology for the device in question, especially in the case of large and very large areas, it is possible to obtain the remote detection of the condition at a large number of points in the soil being analysed, whose number and mutual distance depend on the wireless technology being used and on the criteria adopted for a rational measurement campaign concerning soil fertility. The present specifications of one of the WSN technologies available, the ZigBee technology, include a maximum of over 65,000 modules belonging to a single network and a maximum distance between modules and devices in the open field of approximately 70 m in the standard models and approximately 200 m in the strengthened version.

Furthermore, the function of relay between a node-sensor and the other makes it possible to increase the measurement distance up to a maximum of six repeaters from the furthest node and the receiving station.

Presently said technology would be the most suitable for the remote detection of the condition of the instrument in question and its transmission to a centre node having the function to collect data and manage the network and interfaced with a normal portable PC.

Said modules are characterized by a low data rate but by high autonomy (approx. 1 year with a common stilo battery) and this makes them the ideal solution for use in the context in question, where high data flows are not necessary and the expected permanence in situ is limited to a few weeks.

The reduced size of the WSN components furthermore ensures reduced costs and easy integration in an instrument such as the one that is the subject of this description.

In practice, independently of the wireless technology adopted, the operation of the WSN modules present in the devices requires a permanence in a "stand-by" condition for most of the time, with a minor current consumption, except that it is reactivated for a very short time in order to verify if at the centre supervisor node connected to the portable PC there is a pending data request directed to it.

In this case that module would carry out a hardware routine to verify what indicators are free due to the breakage of their thread located in the ground.

The condition of the indicators, together with the identification code of the device (ID), would be transmitted via radio to the supervisor node that would pass it to the PC connected to it for storage in a simple file, like an Excel file or analogous software.

The software would input the incoming data in a record indexed by ID inside the Excel file already containing the geographical position of the device detected at the moment of its positioning on site through a GPS receiver that may be autonomous or integrated in the portable PC.

Also the date and time of start of operation of each device is automatically input in the same record in order to make comparisons between successive conditions.

The simple database formed in this way can be used for the successive analysis through specifically developed software that in addition to a numerical result can also provide a graphic representation of the level of microbial activity and if necessary of the consequent degree of maturation and/or fertility of the soil according to various procedures useful for making agronomic and management decisions.

One of these is the possibility to display the condition of the soil on a suitable map obtained by integrating and comparing the incoming data received from the devices in the days following their placement in the field.

In fact, having planned the registration of the events that took place, that is, date and time of commissioning of each device and of activation of its indicators, it is possible to obtain useful information regarding the general situation of the microbial activities in the soil being examined.

More specifically, it would be possible to find out whether a portion of soil is more or less active than other ones by simply interrogating the database through the software.

In fact, it is sufficient to implement in it an algorithm that makes the comparisons between events taking place at distinct moments to obtain the final rate of activity in the soil, both properly comparing the time sequence of the activation of the indicators of a device and correlating omologous indicators activated in different devices.

The device that is the subject of the invention can be produced using standard materials and processing cycles, that is, usually available on the market and commonly used in the industry. Mass reproduction of the device is thus possible.

Proposals for suitable materials and components that should be considered as non-limiting examples are listed here below.

The main body, meaning the bar, is constituted by a tubular element (approx. 700 mm long) in a plastic material (PVC, polyethylene or another material) that ensures resistance to weather agents and UV radiation and in any case is suitable for use in the fields. It can be made in a single piece comprising tip, cylindrical body, guide discs for threads and rods, upper section and grip.

The various guide discs serve to maintain the rods and threads in position.

They can be distinct elements obtained from a PVC sheet, holed and mounted on the main body. If produced separately, they can be obtained from a round bar in a plastic material or produced with all the necessary holes through a moulding process. The possibility to produce disc and main body already integrated with a single processing cycle should be taken in consideration. The production of the protective casing that encloses and protects the system of rods and springs substantially requires the cutting of pipes in a plastic material. It consists of two parts: a lower matt one and an upper transparent one to allow the condition of the indicators to be checked. The lower pipe slides so as to ensure access to the lower ends of the rods and easy coupling of the threads to be placed in the soil. The two pipes can be produced also connected to each other or completely independent of each other.

Given the special operation of the rods, to make them it is possible to use common bicycle spokes in 18/8 stainless steel adapted to the purpose through a simple modification of the standard production profile. It is a mechanical detail that already has a particular original configuration at the end that is the ideal solution for coupling the upper part of the threads (eyelet). For correct use in the instrument it is only necessary to make a slight counter fold at the curved end of the original spoke. Said type of processing can be simply performed by resetting a folding parameter of the automatic production equipment. The second fold serves to ensure that the traction force exerted on the filaments acts only along the longitudinal axis of the rods, thus reducing to a minimum any radial forces that would cause undesired friction between them and the guide discs. Said mechanical detail, being mass produced in millions of items by many national and foreign companies, has a negligible unit price and therefore the adoption of this solution would avoid the costs for the production of specific rods.

Finally, they are supplied with the opposite end already threaded, which ensures easy fixing of the coloured indicators.

The indicators are located on the top of the rods and made of a coloured plastic material. Providing the indicators with small magnets to be inserted in their upper base, it is possible to operate micro contacts or Hall effect sensors belonging to an optional detection electric circuit housed in the upper part of the instrument as described below.

The threads to be placed in the soil are provided with ends that can be inserted in the instrument in a rapid manner and with no need for tools, as is visible in the drawings. For this purpose a spherule in a suitable plastic material is fixed through die casting at one end and a small cylinder in the same material is fixed at the other end, where it creates an eyelet suited to be coupled to the lower end of the steel rods. Both the spherules and the cylinders are coloured to allow identification of the type of threads. Their production can be carried out by companies specializing in the moulding of plastic items for the clothing industry, like tags, mark labels, seals etc. that are usually present in new clothes.

For silk or cotton threads the following types of standard fibres have shown to be suitable:
  silk, TRE STELLE, art. 2624, "seta bozzolo reale", title n. 24;
  cotton, TRE STELLE, extra strong, title n. 16.

After the positioning of the threads, the rods are maintained tensioned by means of stainless steel springs locked with screw collars. The springs are commonly produced by specialized companies that produce them in series from standard models or according to the customer's design. Screw collars are commonly available in standard sizes but alternatively it is possible to use more economic standard stop rings with small diameter to be placed along the stainless steel rods in such a position as to guarantee the correct compression of the springs.

The device ends at the top with a cylindrical element serving as a grip for driving it into the soil. In the version with electronic device, it can accommodate the batteries, the antenna of the WSN module, a GPS receiver, if any, a chronometer and the activation switch.

The upper part of the instrument, just below the grip, is provided with guide holes in which the indicator cylinders that are integral with the rods are inserted following the activation of the same. A portion of them remains visible, however, in order to allow the visual check of the condition of the threads, at least for a certain distance.

However, if the device is provided with a detector electronic circuit, its shape and dimensions can be changed in the production phase based on the actual overall dimensions of said circuit. Said optional circuit should be dedicated to the electronic detection of the condition of the indicators through the reading of the on-off state of the micro contacts (for example, Reed contacts or Hall sensors), operated by the magnets with which the indicators are provided and placed in a suitable position inside the structure itself.

The electronic components used for this instrument, in addition to detecting the condition of the indicators, provide for storing an identification code (ID, to be set through a software utility) and the data of a RTC (real time clock) circuit that supplies the time data (dd-hh-mm).

Using a microprocessor, said electronic system makes it possible to implement other useful functions in the device, such as the autonomous determination of the position through a low cost GPS module or the interfacing with a LOC (Laboratory on Chip) module and sensors for measuring the temperature of the soil/biomass, the humidity, the developed gases etc.

In particular, the LOC module, which is the product of the evolution of micro electronics and is available at acceptable prices, would make it possible to carry out chemical analyses directly on site on the gaseous metabolites produced by the micro-organisms present in the active substrate ($H_2$, $H_2S$, $CO_2$, $CH_4$, $C_2H_4$, NO, $N_2O$, $NH_3$, $CH_4$ etc.) which is then translated in the possibility to follow the evolution of the substrate over time, integrating the supplied data with the time data of the RTC module and the temperature/humidity parameters. LOC modules for carrying out various types of analyses are already available on the market.

The electronic components provided on the device are completed by a WSN (Wireless Sensor Network) module intended to maintain the wireless remote communications with the receiving station (WSN supervisor/coordinator) interfaced with a PC.

The remote collection of the data received from instruments/sensors requires their processing with an application software that should initialize the entire network of devices present on the field and periodically check their condition for the suitable data processing necessary for final rendering, that is, graphic representation on a monitor of the microbial dynamics in the soil or the other subjects being analysed. This presentation must be carried out in such a way as to provide a concise and rational view of the situation detected by the sensors to the users, independently of whether they are specialists or farmers. Using more advanced versions of the device it would be possible to provide the territory with a sort of nervous system capable of constantly monitoring the microbiological dynamics, bringing in new knowledge that can be a support when it comes to making the most suitable agronomic and management decisions.

A test that involved 10 vineyards clearly shows that the method proposed by the invention can be applied for the assessment of the level of microbial activity and the consequent fertility of the soil even in terms of grape yield. The table below sums up correlation data between the thread biodegradation parameters and the organic substance, the C/N ratio and the productivity in quintals of harvested grapes.

The contents of organic substance at 0-30 cm are correlated with the degradation of the control silk thread while the contents at 30-60 cm present significant correlations with the degradation of both cotton treated with nitrogen and control silk. Also the C/N ratio at 0-30 cm is correlated with the degradation of the control silk thread while the C/N ratio at 30-60 cm presents significant correlations both with the degradation of both cotton treated with nitrogen and control silk. Productivity has shown to be correlated with the degradation of cotton and silk in the control tests and of cotton treated with nitrogen. The higher correlation coefficients have been found to exist between the C/N ratio at 30-60 cm and the degradation of silk in the control test.

TABLE

Correlations between microbial activity (% degradation of the filaments), organic substance, C/N ratio and productivity

| | Cotton degradation | | | Silk degradation | | |
|---|---|---|---|---|---|---|
| | Control | Nitrogen | Phosphorus | Control | Nitrogen | Phosphorus |
| Organic substance (0-30 cm) | n.s. | n.s. | n.s. | 0.650* | n.s. | n.s. |
| Organic substance (30-60 cm) | n.s. | 0.667* | n.s. | 0.706* | n.s. | n.s. |
| C/N ratio (0-30 cm) | n.s. | n.s. | n.s. | 0.747** | n.s. | n.s. |
| C/N ratio (30-60 cm) | n.s. | 0.733** | n.s. | 0.803** | n.s. | n.s. |
| Productivity | 0.774** | 0.697* | n.s. | 0.792** | n.s. | n.s. |

(*$p < 0.05$;
**$p < 0.01$;
ns: not significant).

The analysis clearly shows how the degradation of silk and cotton can become a useful index of the microbial activity and fertility of the soil.

Upon implementation, the method, the device and the kit for the assessment of is the level of microbial activity of a substrate that are the subjects of the invention can be subjected to further modifications and variant embodiments can be obtained that are not described herein. Said changes or variants must all be considered protected by the present patent, provided that they fall within the scope of the claims expressed below.

Where technical features mentioned in any claim are followed by reference signs, those reference signs have been included for the sole purpose of increasing the intelligibility of the claims and accordingly such reference signs do not have any limiting effect on the protection of each element identified by way of example by such reference signs.

The invention claimed is:

1. A method for assessing a level of microbial activity of a soil substrate, the method comprising:
   a) preparing one or more biodegradable threads;
   b) tensioning said one or more biodegradable threads with a pre-defined tension;
   c) introducing said one or more tensioned biodegradable threads at least partially in said soil substrate;
   d) leaving said one or more tensioned biodegradable threads in said soil substrate; and
   e) measuring a time elapsed from the introduction of said one or more tensioned biodegradable threads in said soil substrate to a breakage of said one or more tensioned biodegradable threads.

2. The method according to claim 1, wherein at least two threads of said one or more biodegradable threads are made of a different material.

3. The method according to claim 1, wherein said one or more biodegradable threads are of protein or vegetable origin.

4. The method of claim 3, wherein the biodegradable threads are of cotton or silk origin.

5. The method according to claim 1, wherein for at least one of said one or more biodegradable threads there is at least another biodegradable thread made of an identical material provided with at least one fertilizer substance, the method further comprising determining a lack or excess of this fertilizer substance in said substrate through a comparison of the breaking time of these two threads.

6. The method according to claim 5, wherein said fertilizer substance is selected from a group constituted by mineral sources of nitrogen, phosphorus, potassium, calcium, magnesium, sulphur and other meso and microelements.

7. The method of claim 1, further comprising leaving said one or more tensioned biodegradable threads in said substrate until at least one of said one or more tensioned biodegradable threads breaks.

8. The method of claim 7, further comprising measuring the time elapses from the introduction of said one or more tensioned biodegradable threads in said substrate until said at least one of said one or more tensioned biodegradable threads breaks.

9. A device for assessing a level of microbial activity of a substrate comprising:
   one or more biodegradable threads;
   a first fixing element for each of the one or more biodegradable threads;
   a second fixing element for each of the one or more biodegradable threads;
   for each biodegradable thread, an indicator suited to signal a breakage of the thread, each said indicator being integral and therefore movable with said second fixing element and suited to signal any breakage of the thread through its position;
   for each biodegradable thread, a first end is fixed in the first fixing element and a second end is fixed in the second fixing element,
   wherein the first fixing element and the second fixing element are configured such that each biodegradable thread can be independently tightened with a pre-defined tension.

10. The device according to claim 9, further comprising one or more tensioning elements suited to exert a given traction force on said one or more biodegradable threads in order to obtain said pre-defined tension of said threads.

11. The device according to claim 9, wherein for at least one biodegradable thread there is at least another biodegradable thread made of an identical material provided with at least one fertilizer substance and/or there are at least two biodegradable threads made of a different material.

12. The device according to claim 9, wherein a base structure of said device is a bar that for each biodegradable thread is provided in its lower part with said first fixing element and, axially spaced from said first fixing element, with a separating element housing, in an axially moving form for each thread a rod whose first end, which is on the side of the separating element facing towards the first fixing element, is provided with said second fixing element and along whose length, on the other side of the separating element, there is a spacer integral with said rod, and wherein said spring is coaxially inserted in said rod enclosed between said spacer and said separating element, in such a way that fixing said thread between said first and said second fixing element means tensioning the thread and compressing the spring between the spacer and the separating element, and in case of breakage of the thread the spring expands, thus moving the rod whose second end is said indicator that by moving together with the rod signals the breakage of the thread through its new position.

13. The device according to claim 9, wherein the device is a measuring device for the soil.

14. The device according to claim 13, wherein said second fixing element can be moved with respect to said first fixing element, and wherein said tensioning element is a spring that exerts said traction force on said second fixing element so that a biodegradable thread tightened between the first fixing element and the second fixing element loads the spring that, in case of breakage of the thread, moves the second fixing element away from the first fixing element and returns the spring to an unloaded position.

15. A device for assessing a level of microbial activity of a substrate comprising:
   one or more biodegradable threads;
   a first fixing element for each of the one or more biodegradable threads;
   a second fixing element for each of the one or more biodegradable threads;
   for each biodegradable thread, a first end is fixed in the first fixing element and a second end is fixed in the second fixing element,
   wherein the first fixing element and the second fixing element are configured such that each biodegradable thread can be independently tightened with a pre-defined tension,
   wherein said second fixing element can be moved with respect to said first fixing element, and wherein said tensioning element is a spring that exerts said traction force on said second fixing element so that a biodegradable thread tightened between the first fixing element and the second fixing element loads the spring that, in case of breakage of the thread, moves the second fixing element away from the first fixing element and returns the spring to an unloaded position, and
   wherein the device is a measuring device for soil.

* * * * *